United States Patent
Cinbis et al.

(10) Patent No.: US 9,867,990 B2
(45) Date of Patent: Jan. 16, 2018

(54) DETERMINATION OF DIPOLE FOR TISSUE CONDUCTANCE COMMUNICATION

(75) Inventors: Can Cinbis, Shoreview, MN (US); David A. Anderson, Stanchfield, MN (US); Michael A. Reinert, St. Cloud, MN (US); Xiaonan Shen, Shoreview, MN (US); James K. Carney, Brooklyn Park, MN (US); Michael B. Terry, Camas, WA (US)

(73) Assignee: Medtronic, Inc., Minneapolis, MN (US)

( * ) Notice: Subject to any disclaimer, the term of this patent is extended or adjusted under 35 U.S.C. 154(b) by 398 days.

(21) Appl. No.: 12/915,788

(22) Filed: Oct. 29, 2010

(65) Prior Publication Data

US 2012/0109258 A1 May 3, 2012

(51) Int. Cl.
| | |
|---|---|
| *A61N 1/40* | (2006.01) |
| *A61N 1/372* | (2006.01) |
| *A61B 5/00* | (2006.01) |
| *A61N 1/08* | (2006.01) |
| *H04B 13/00* | (2006.01) |

(52) U.S. Cl.
CPC ........ *A61N 1/37217* (2013.01); *A61B 5/0028* (2013.01); *A61N 1/08* (2013.01); *H04B 13/005* (2013.01)

(58) Field of Classification Search
CPC ............ A61N 1/37288; A61N 1/37211; A61N 1/37229; A61B 5/0031; A61B 5/7221; A61B 5/0026; A61B 5/0028

USPC ................................................ 607/30–32, 60
See application file for complete search history.

(56) References Cited

U.S. PATENT DOCUMENTS

| | | |
|---|---|---|
| 4,987,897 A | 1/1991 | Funke |
| 5,113,859 A | 5/1992 | Funke |
| 5,697,377 A | 12/1997 | Wittkampf |
| 5,983,126 A | 11/1999 | Wittkampf |
| 6,315,719 B1 | 11/2001 | Rode et al. |
| 6,409,674 B1 | 6/2002 | Brockway et al. |
| 6,496,715 B1 | 12/2002 | Lee et al. |
| 6,636,769 B2 | 10/2003 | Govari et al. |
| 6,644,321 B1 | 11/2003 | Behm |
| 6,675,045 B2 | 1/2004 | Mass et al. |
| 6,699,200 B2 | 3/2004 | Cao et al. |
| 6,704,602 B2 | 3/2004 | Berg et al. |
| 7,313,441 B2 | 12/2007 | Mass et al. |
| 7,392,090 B2 | 6/2008 | Sweeney et al. |
| 7,512,448 B2 | 3/2009 | Malick et al. |
| 7,613,522 B2 | 11/2009 | Christman et al. |
| 7,668,596 B2 | 2/2010 | Von Arx et al. |
| 7,672,731 B2 | 3/2010 | Dublin et al. |
| 7,742,816 B2 | 6/2010 | Masoud et al. |
| 7,949,404 B2 | 5/2011 | Hill |

(Continued)

*Primary Examiner* — Niketa Patel
*Assistant Examiner* — Minh Duc Pham

(57) ABSTRACT

Aspects of the present disclosure include a medical device system including an implantable medical device and an external device with three or more electrodes configured to contact a patient's skin. The external device either transmits or receives a test signal to or from the implantable medical device using a plurality of possible receive dipoles, where each possible receive dipole is formed by a pair of electrodes. A signal quality monitor, either at the implantable medical device or at the external device, measures a signal quality for the possible receive dipoles.

23 Claims, 9 Drawing Sheets

(56) References Cited

U.S. PATENT DOCUMENTS

| | | |
|---|---|---|
| 7,991,467 B2 | 8/2011 | Markowitz et al. |
| 8,175,716 B2 | 5/2012 | Rahman et al. |
| 8,352,040 B2 | 1/2013 | Von Arx et al. |
| 8,369,961 B2 | 2/2013 | Christman et al. |
| 8,515,559 B2 | 8/2013 | Roberts et al. |
| 8,934,987 B2 | 1/2015 | Stahmann et al. |
| 8,942,818 B2 | 1/2015 | Markowitz et al. |
| 9,636,511 B2 | 5/2017 | Carney et al. |
| 2002/0099423 A1 | 7/2002 | Berg et al. |
| 2003/0189488 A1 | 10/2003 | Forcier et al. |
| 2004/0199222 A1* | 10/2004 | Sun et al. ............ 607/60 |
| 2006/0142820 A1* | 6/2006 | Von Arx ............ A61N 1/37229 607/60 |
| 2006/0161213 A1 | 7/2006 | Patel |
| 2006/0173265 A1* | 8/2006 | Kim ............ A61B 1/041 600/407 |
| 2007/0268144 A1 | 11/2007 | Dobosz |
| 2008/0046037 A1 | 2/2008 | Haubrich et al. |
| 2008/0234784 A1* | 9/2008 | Li ............ A61N 1/37223 607/60 |
| 2011/0213260 A1 | 9/2011 | Keel et al. |
| 2012/0095744 A1 | 4/2012 | Rahman et al. |

\* cited by examiner

DETERMINATION OF DIPOLE FOR TISSUE CONDUCTANCE COMMUNICATION

TECHNICAL FIELD

This disclosure relates generally to implantable medical device (IMD) systems, and more particularly, this disclosure relates to a system and method for wireless communication using tissue conductance communication (TCC) between an external device and an arbitrarily implanted IMD.

BACKGROUND

IMDs are used to treat patients suffering from a variety of conditions. IMDs can be utilized in a variety of applications such as therapy delivery and monitoring physiological parameters in patients. Some IMDs are designed to generate and deliver electrical pulses to stimulate body tissue, muscles, nerves, brain cells, body fluid, or the like. Uses for IMDs can be found in many different areas of medicine such as cardiology, endocrinology, hematology, neurology, muscular disorders, gastroenterology, urology, ophthalmology, otolaryngology, orthopedics, and similar medical subspecialties.

Examples of IMDs used in cardiac applications are implantable pacemakers and implantable cardioverter-defibrillators. Such electronic medical devices generally monitor the electrical activity of the heart and provide electrical stimulation to one or more of the heart chambers when necessary. For example, pacemakers are designed to sense arrhythmias, i.e., disturbances in heart rhythm, and, in turn, provide appropriate electrical stimulation pulses at a controlled rate to selected chambers of the heart in order to correct the arrhythmias and restore the proper heart rhythm. The types of arrhythmias that may be detected and corrected by such IMDs include bradycardias (unusually slow heart rates) and certain tachycardias (unusually fast heart rates). Some IMDs monitor the electrical activity of the heart, but do not provide electrical stimulation.

Other IMDS may be used to monitor one or more hemodynamic characteristics of a patient, such as the pressure of blood within a particular vessel or chamber of the heart, the oxygen saturation level of blood of the patient (e.g., arterial blood), the volume of blood supplying a particular tissue site, and the like. Example medical devices that monitor hemodynamic characteristics of a patient include pressure sensors, pulse oximeters, blood flow sensors, hematocrit sensors, and tissue perfusion sensors. The pressure indicated by an implanted pressure sensor may be compared to an external pressure to determine gauge pressure of a body fluid, e.g., blood. One type of pressure sensor is a capacitive pressure sensor. One type of pulse oximeter includes at least one light source that emits light through a portion of blood-perfused tissue of a patient, and an optical detector that senses the emitted light that passed through the blood-perfused tissue. The time-varying optical amplitude measured by the optical detector can be processed, using algorithms known by those skilled in the art, to produce a measure of arterial blood oxygen saturation of the patient.

SUMMARY

TCC, as known in the art, has not been a viable alternative to RF telemetry for communicating with certain types of IMDs. Electric field strength is inversely proportional to the cube of the distance away from a transmitter, thus causing rapid signal attenuation when an IMD is deeply implanted. Thus, to successfully implement TCC as presently known, either the transmit and receive devices need to be located only a short distance apart or the transmit device needs to transmit a strong signal. Short transmit distances, however, are not always an option because of desired implant locations, and transmitting a strong signal is often not compatible with the limited battery capacity of many modern, smaller IMDs, especially IMDs that are deeply implanted which tend to be smaller than non-deeply implanted IMDs. The present disclosure describes techniques for tissue conductive communication (TCC). The techniques, in some examples, may involve selection of one of a plurality of dipoles, formed by electrodes positioned at different positions, that provides a desirable signal quality for communication with an implantable medical device. These techniques, by selecting a dipole that provides a desirable signal quality, may permit the IMD to support reliable transmission of signals at a lower signal strength. In some examples, such techniques also may aid a user in identifying a particular external device type that works well in providing TCC for a particular implant scenario.

In one example, an external device includes a plurality of electrodes positionable at different tissue contact points on an external tissue surface of a patient; a communication unit configured to communicate with an implantable medical device via a plurality of dipoles formed by different combinations of the electrodes; and a processor configured to identify a dipole that provides at least a minimum signal quality with the implantable medical device.

In another example, an implantable medical device comprising includes a communication receiving unit configured to receive, from an external device, a plurality of test signals via a plurality of dipoles formed by different combinations of electrodes, the electrodes being from a plurality of electrodes positionable at different tissue contact points on an external tissue surface of a patient; identify within each test signal, a signal identification for the test signals; a signal quality monitor configured to determine a signal quality for each test signal; and a communication transmitting unit configured to transmit, to the external device, an indicator of at least one signal identification for at least one test signal.

In another example, a medical device system comprising includes an implantable medical device (IMD) with a first communication unit and a first processor; as well as an external device with a plurality of electrodes positionable at different tissue contact points on an external tissue surface of a patient; a second communication unit configured to communicate with the IMD via a plurality of dipoles formed by different combinations of the electrodes; and a second processor configured to identify a dipole that provides at least a minimum signal quality with the IMD.

In another example. a method comprises communicating with an implantable medical device (IMD) via a plurality of dipoles formed by different combinations of electrodes positioned at different tissue contact points on an external tissue surface of a patient; and identifying a dipole that provides at least a minimum signal quality with the implantable medical device.

The details of one or more embodiments of the invention are set forth in the accompanying drawings and the description below. Other features, objects, and advantages of the invention will be apparent from the description and drawings, and from the claims.

DETAILED DESCRIPTION

Existing IMDs are typically capable of supporting wireless telemetry through inductive or radio frequency (RF) transmission, with an external programmer or an interface device that can transfer IMD data to a computer-based diagnostic or monitoring application. As device sizes shrink, however, communication between external instruments and the IMD using telemetry becomes more challenging because the size of an IMD's antenna is restricted, resulting in a significant decrease in the amplitude of the signal that the IMD can transmit or receive. Adding to the challenges of standard telemetry is a desire to implant these smaller devices deeper into patients. While deeper implantation can allow devices to monitor or stimulate harder to reach portions of the body, it further complicates the use of traditional telemetry because of large signal attenuation as RF energy passes through thick layers of body tissue.

The present disclosure describes techniques for tissue conductive communication (TCC). The techniques, in some examples, may involve selection of one of a plurality of dipoles, formed by electrodes positioned at different positions, that provides a desirable signal quality for communication with an implantable medical device. These techniques, by selecting a dipole that provides a desirable signal quality, may permit the IMD to support reliable transmission of signals at a lower signal strength. In some examples, such techniques also may aid a user in identifying a particular external device type that works well in providing TCC for a particular implant scenario.

Figure 1:
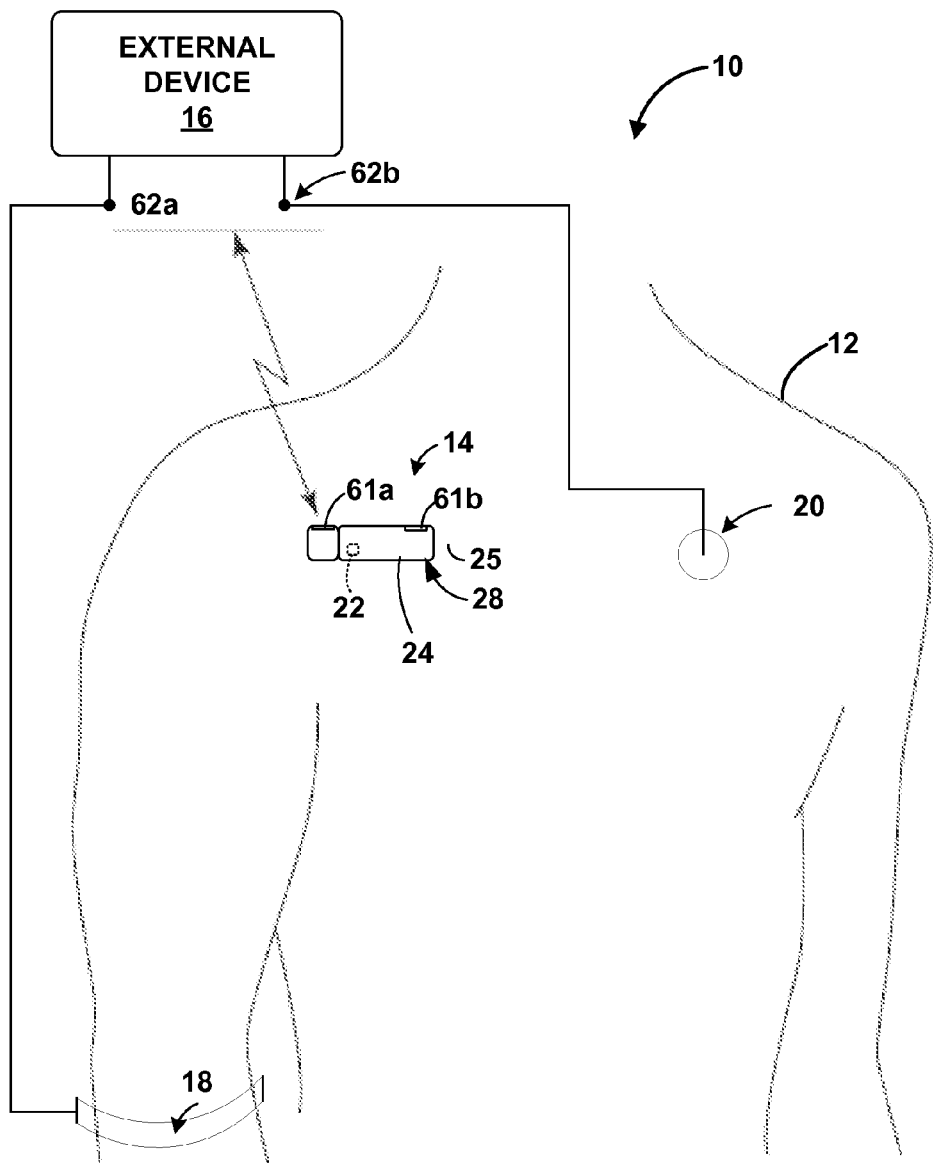
FIG. 1 is a conceptual diagram illustrating an example system that includes an implantable medical device (IMD) configured to communicate via TCC with an external device.

FIG. 1 is a conceptual diagram illustrating an example monitoring system 10 that may be used to monitor one or more physiological parameters of patient 12, such as a pressure and/or an oxygen saturation level of blood of patient 12 or other hemodynamic characteristics of patient 12. Patient 12 ordinarily, but not necessarily, will be a human. Monitoring system 10 includes implantable medical device (IMD) 14 and external device 16. IMD 14 may be an implantable monitor, such as a pressure sensor that does not provide therapy to patient 12. In some examples, other embodiments, IMD 14 may alternatively or additionally be configured to provide therapy, such as electrical stimulation therapy or delivery of a therapeutic agent, to patient 12. Although specific types of medical devices and specific functionality may be referenced in this disclosure for purposes of explanation, the techniques described are not limited to any particular type of IMD. Neither IMD 14, external device 16, nor any of the figures shown in this disclosure are necessarily drawn to any particular scale. The techniques of this disclosure may include numerous advantages when implemented in systems including relatively small IMDs and deeply implanted IMDs. As examples, a small IMD can have a volume of less than one cubic centimeter, and a deeply implanted IMD might be implanted anywhere from 5 to 20 centimeters deep in a patient, relative to an exterior skin surface of the patient.

In the example shown in FIG. 1, IMD 14 is implanted within a subcutaneous tissue layer of patient 12. Due to its relatively small size, a clinician may implant IMD 14 through a relatively small incision in the patient's skin, or percutaneously, e.g., via an introducer. In other examples, IMD 14 may be implanted within other tissue sites, such as a submuscular location, or within a blood vessel, a chamber of the heart, the bladder, the gastrointestinal tract, or the brain. IMD 14 may be a temporary diagnostic tool employed to monitor one or more physiological parameters of patient 12 for a relatively short period of time (e.g., days or weeks), or may be used on a more permanent basis. In some cases, IMD 14 may be used to control therapy delivery to patient 12. In some examples, a separate therapy delivery device, such as a fluid delivery device, pacemaker, cardioverter-defibrillator, or neurostimulator, may be implanted within patient 12. The therapy delivery device may communicate with IMD 14 via a wired connection or via wireless communication techniques. In other examples, as previously described, IMD 14 may be incorporated in a common housing with a therapy delivery device.

IMD 14 comprises electrodes 61*a* and 61*b* connected to a communication module within IMD 14 for sending and receiving data to and from external device 16. Electrodes 61*a-b* may also be used for purposes other than sending and receiving data, such as electrically monitoring a physiological signal (e.g., cardiac electrogram (EGM) signals, electrocorticographic (ECoG) signals, or electroencephalographic (EEG) signals) or delivering stimulation therapy. Electrodes 61*a-b* may be positioned any suitable distance from each other. For example, in a small IMD, electrodes 61*a* and 61*b* may be separated by approximately 5 mm. In the example shown in FIG. 1, electrodes 61*a-b* are electrically coupled to an outer housing 24 of IMD 14. In other examples, electrodes 61*a-b* may be coupled to leads that extend from outer housing 24 of IMD 14. In some examples, housing 24 may comprise a biocompatible and hermetic housing. Case 28 may be hermetically sealed and may enclose various sensing and control circuitry for sensing one or more physiological parameters of patient 12, and, in some cases, a therapy delivery module for delivering therapy to patient 12 (e.g., electrical stimulation or a therapeutic agent).

IMD 14 may be useful for monitoring physiological parameters of patient 12, and as described in further detail below with reference to FIG. 3, IMD 14 may include a memory 34 that stores data related to the physiological parameters monitored by the IMD 14. In addition or alternatively, IMD 14 may transmit, via TCC, information to an external device, such as external device 16, an example of which is shown in more detail at FIG. 4. In other examples, the clinician (or other user) may interrogate IMD 14 with external device 16 via TCC while IMD 14 remains implanted within patient 12 in order to retrieve stored information from IMD 14. The physiological parameter values monitored by IMD 14 may provide useful information for diagnosing a patient condition or formulating a treatment plan for patient 12.

External device 16 includes electrodes 62a-62b that connect to a communication module within external device 16 for sending and receiving data to and from IMD 14. In the example of FIG. 1, electrode 62a makes contact with tissue of patient 12 via a conductive wrist band 18, and electrode 62b makes contact with tissue of patient 12 via a patch 20, e.g., such as an electrocardiograph (ECG) patch, connected to the chest of patient 12. Patch 20 and wrist band 18 are just two examples of conductive structures that could be used to make contact with patient 12. As will be illustrated, this disclosure contemplates numerous alternative conductive structures being used either in conjunction with or in lieu of patch 20 and wrist band 18.

External device 16 may be a handheld computing device or a computer workstation. External device 16 may include a user interface that receives input from a user, such as a clinician. The user interface may include, for example, a keypad and a display, which may for example, be a cathode ray tube (CRT) display, a liquid crystal display (LCD) or LED display. The keypad may take the form of an alphanumeric keypad or a reduced set of keys associated with particular functions. External device 16 can additionally or alternatively include a peripheral pointing device, such as a mouse, via which a user may interact with the user interface. In some embodiments, a display of external device 16 may include a touch screen display, and a user may interact with external device 16 via the display.

A user, such as a physician, technician, or other clinician, or the patient, may interact with external device 16 to communicate with IMD 14. For example, the user may interact with external device 16 to retrieve physiological or diagnostic information from IMD 14. A user may also interact with external device 16 to program IMD 14, e.g., select values for operational parameters of monitor 14.

The electrodes 61a-b of IMD 14 can form both a receive dipole and a transmit dipole, and electrodes 62a and 62b of external device 16 can form both a receive dipole and a transmit dipole, each for use in TCC. A transmit dipole injects modulated electrical current into the tissue of patient 12, and a receive dipole, also in contact with tissue of patient 12, receives the modulated signal as an electric potential difference across the pair of electrodes. Accordingly, external device 16 and IMD 14 can communicate bi-directionally via the TCC techniques described herein. For example, the user may use external device 16 to retrieve information from IMD 14 related to the health of patient 12, use external device 16 to retrieve information from IMD 14 regarding the performance or integrity of IMD 14, or use external device 16 to program IMD 14.

The electrodes 61a-b of IMD 14 and the electrodes 62a and 62b of external device 16 can each be configured to function as a dipole antenna and transmit and receive information encoded in electrical signals. For example, information relating to monitored physiological parameters of patient 12 can be stored in a memory 34 of IMD 14 and periodically transmitted to external device 16. Information can also be transmitted in the opposite direction (i.e. from the external device 16 to IMD 14), for example, when external device 16 provides programming information to IMD 14. Aspects of the present disclosure include facilitating communication between external device 16 and IMD 14 over frequencies ranging from a few kilohertz to a few megahertz. Higher frequency communication signals may be used to increase data transmission rates.

Figure 2A:
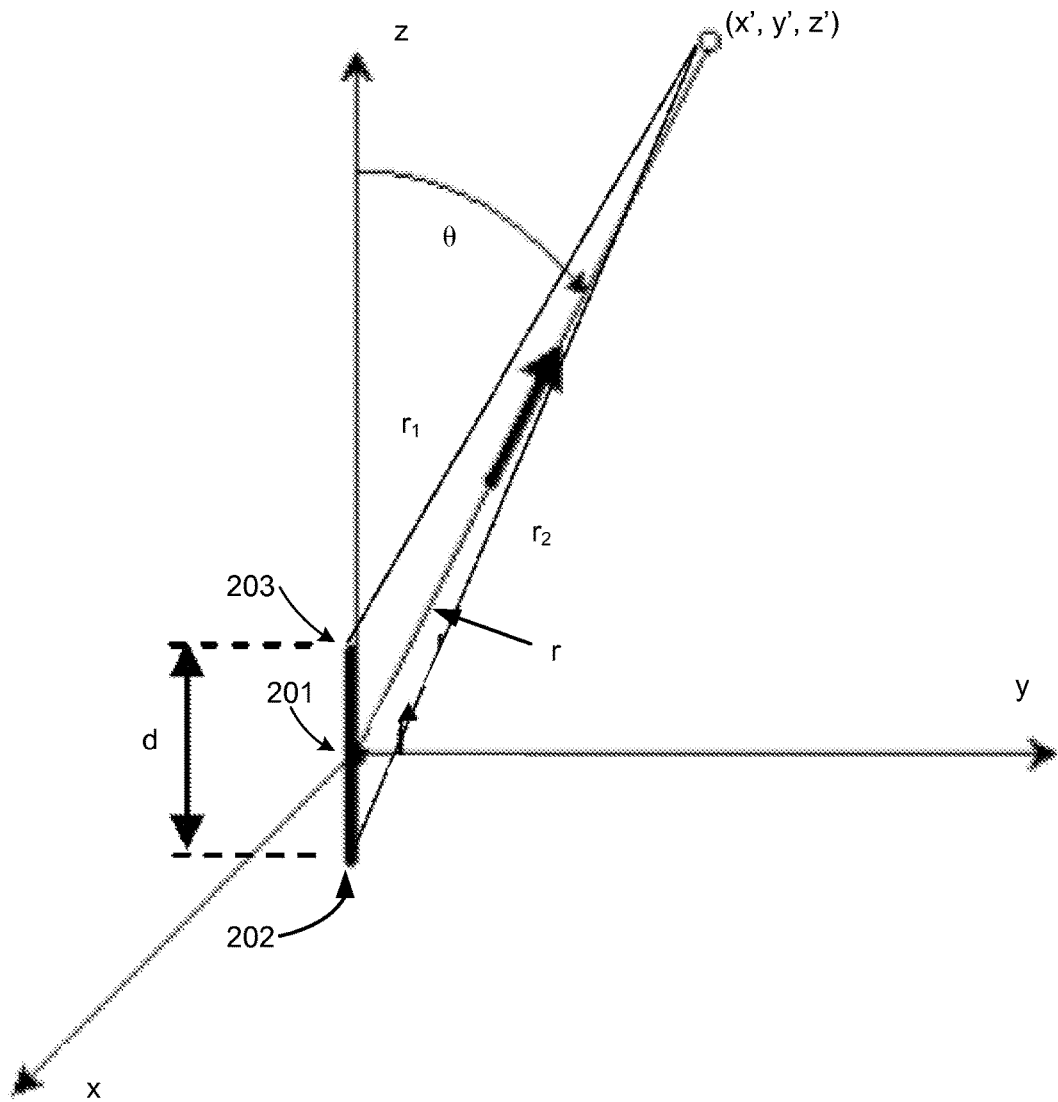
FIGS. 2*a* and 2*b* are graphs illustrating the effects geometry has on send and receive dipoles.

The electric potential at a point in space with coordinates, x', y' and z' due to an infinitesimally thin current dipole is shown at FIG. 2a and described by equation 1, as follows:

$$\phi = \frac{I_o}{4\pi\sigma}\left(\frac{1}{r_1} - \frac{1}{r_2}\right) \quad (1)$$

Where φ is the potential, Io is the dipole current, σ is the conductivity of the surrounding medium, r1 is the distance between observation point (x', y', z') and current source end 203 of the dipole 201, and $r_2$ is the distance between observation point (x', y', z') and the current sink end 202 of the dipole 201. Assuming for this example that IMD 14 sends data to external device 16, the current source end 203 of the dipole 201 is an electrode of IMD 14, such as electrode 61a. The current sink end 202 of the dipole 201 is the other electrode 61b of IMD 14. Thus, r1 equals the distance through the body from electrode 61a to the observation point, which might for example be patch 20 connected to the chest of patient 12, and r2 equals the distance through the body from electrode 61b to patch 20 connected to the chest of patient 12. At patch 20, a first electric potential (φ1) is detected. Using the same equation, a second electric potential (φ2) can be detected at wrist band 18. Thus, the signal received by external device 16 at electrodes 62a and 62b corresponds to the electric potential difference φ1−φ2.

Figure 2B:
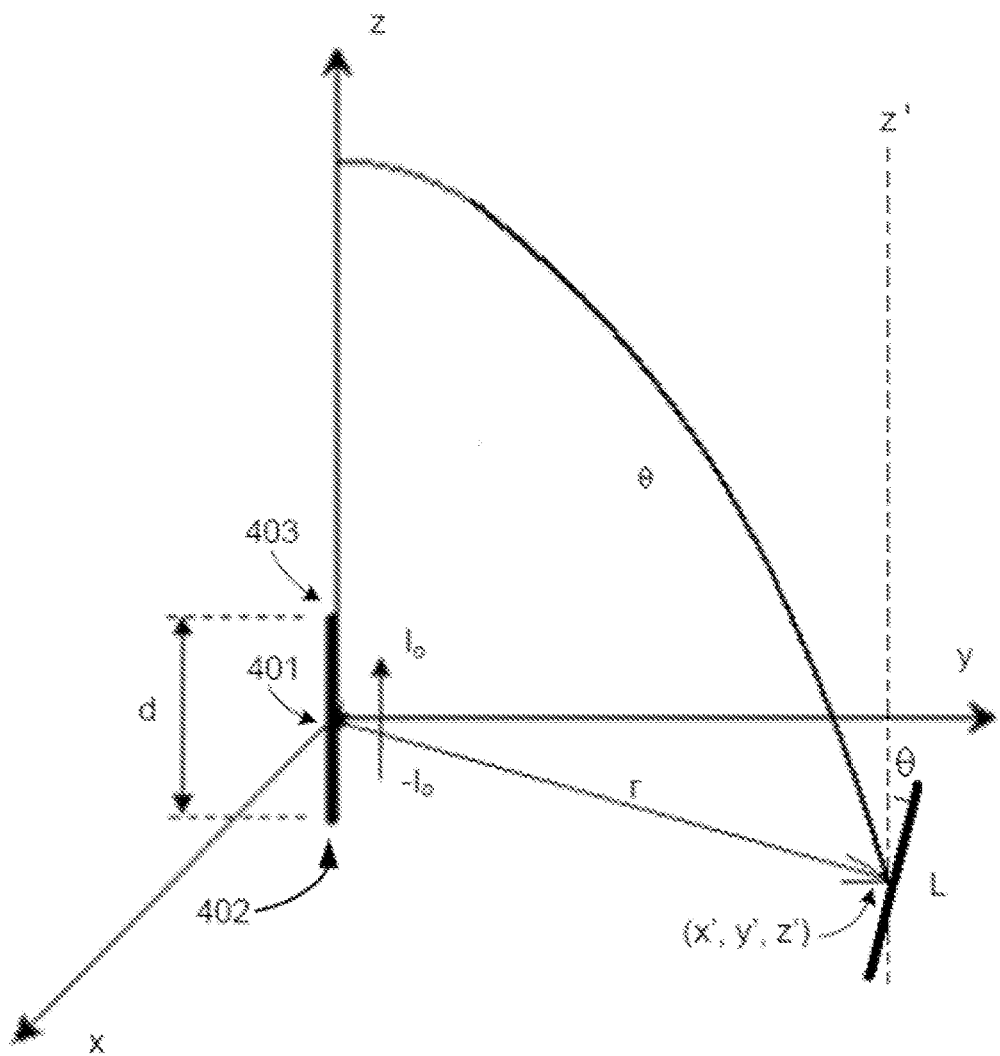

As shown by the diagram of FIG. 2b, if r>>d, where d equals the transmit dipole length, then the electric potential at a point in space can be approximated by equation 2, as follows:

$$\phi = \frac{I_o \cdot d}{4\pi\sigma r^2}\cos\theta \quad (2)$$

where r is the distance between the observation point and the center of the dipole and θ is the polar angle. The polar angle generally refers to the angle between the line depicting the axis of dipole 201 and the line drawn from the center of dipole 201 to one of the receive electrode positions. The value of d corresponds to the distance between electrode 61a and electrode 61b, which depending on the size of IMD 14 might be as small as 5 mm or as large as 500 mm, if one of electrode 61a or 61b is extended from the housing of IMD 14 using a lead, for example. If there is a receive dipole of length L with each end equi-distant from the center of the current dipole with half of the receive dipole above the x-y plane, and having an angle of orientation (θ) with respect to the current dipole, received electric potential difference, $V_{RX}$ can be calculated by equation 3, as follows:

$$V_{RX} = \frac{I_o \cdot d \cdot L}{4\pi\sigma}\frac{1}{(r^2 + L^2/4)^{3/2}}\cos(\theta) \quad (3)$$

As shown, by equations 2 and 3, the signal received by external device 16 at electrodes 62a and 62b, which corresponds to the voltage difference ø1−ø2, is a function of the length of the transmitting dipole (d), the length of the receive dipole (L), and the angle of orientation (θ) between the transmit dipole and receive dipole. The length of the transmitting dipole (d) is typically a fixed value constrained by the size of IMD 14. The length of the receive dipole (L) and the angle of orientation (θ), however, are variables that can be altered based on the location at which electrodes 62a and 62b of external device 16 make contact with patient 12. As implant locations and orientations vary and the geometries of individual patients vary, no one single receive dipole will be optimal for all implant scenarios or will even necessarily be functional for all implant scenarios. Additionally, at certain orientations, external device 16 might not be able to detect a transmit signal from IMD 14 at all, which is sometimes referred to as a null orientation, e.g. when θ=90°. Aspects of the present disclosure include determining a signal quality for a plurality of receive dipoles so that null orientations can be avoided and optimal receive dipoles can be determined.

As used in this disclosure, an optimal receive dipole may refer to the receive dipole, as defined by the two contact points on a patient, that provides the highest signal quality, but what constitutes optimal may also be determined based on other metrics. For example, a receive dipole that provides adequate enough signal quality for establishing a reliable communication session and that enables the external device 16 to be used by a user in an ergonomical manner may be the optimal receive dipole even if it does not produce the highest signal quality.

Signal quality as used in this disclosure may be assessed using a variety of methods including but not limited to a transmission power required for signal detection, a received signal strength, a received signal-to-noise ratio, a bit error rate, a data throughput rate, a data dropout rate, a background noise floor, an optimum frequency, a correlation between a detected signal and a known template for a signal, or any combination of these measures.

Figure 3:
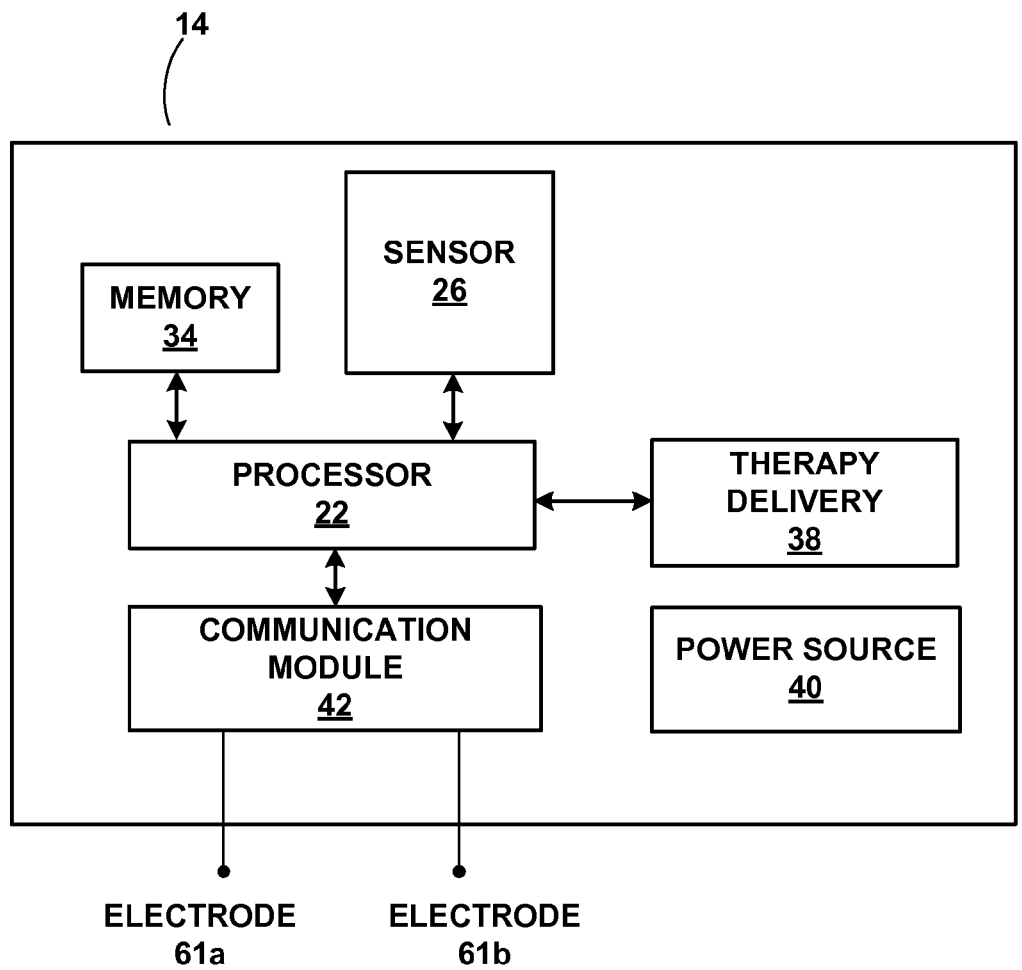
FIG. 3 is a block diagram illustrating an example of an IMD configured to communicate bi-directionally with an external device via TCC.

FIG. 3 is a functional block diagram illustrating components of an example of IMD 14, which includes processor 22, memory 34, a sensor 26, a power source 40, and a communication module 42 comprising two electrodes 61a-b. IMD 14 may include any number and type of sensors, and need not include therapy delivery mechanisms 38, depending on the type of device.

Processor 22 may control the operation of sensor 26 and therapy delivery mechanism 38 with the aid of instructions associated with program information stored in memory 34. For example, the instructions may define the timing of therapy delivery, waveform characteristics for electrical stimulation, and/or dosing programs that specify an amount of a therapeutic agent to be delivered to a target tissue site within patient 12. Components described as processors within IMD 14 and external device 16 may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Memory 34 may include any volatile or non-volatile media, such as a random access memory (RAM), read only memory (ROM), non-volatile RAM (NVRAM), electrically erasable programmable ROM (EEPROM), Flash memory, and the like. As mentioned above, memory 34 may store program information including instructions for execution by processor 22, which may cause processor 22 and IMD 14 to provide the functionality described herein. The instruction may include therapy programs, which may be instructions for the operation of therapy delivery mechanism 38, and any other information regarding therapy of patient 12. In addition, memory 34 may store instructions for the operation of sensor 26. Memory 40 may also store device and patient information, which may include information regarding the operation and integrity of IMD 14 or any of its components, as well as physiological information regarding patient, e.g., derived from the signal or data provided by sensor 26. Memory 40 may include separate memories for storing instructions, patient information, therapy parameters, therapy adjustment information, program histories, and other categories of information such as any other data that may benefit from separate physical memory modules.

Communication module 42 in IMD 14 is coupled to a pair of electrodes 61a-b configured to function as an electric dipole and transmit and receive information encoded in electrical signals to and from external device 16. In some configurations, communication module 42 may also be configured to operate as a signal quality monitor and assess the signal quality of an electrical signal received from external device 16. These electrical signals are typically transmitted in a modulated format such as frequency shift keying, amplitude shift keying, phase shift keying, pulse width modulation, pulse amplitude modulation, quadrature amplitude modulation, orthogonal frequency division multiplexing, spread spectrum techniques, or in an analog signal format and/or modulation technique such as analog amplitude modulation or frequency modulation. In one example, processor 22 controls communication module 42 to send and receive the information. In some embodiments, the communication module 42 of IMD 14 can be configured to operate for periods of time in a sleep state in order to conserve battery power. In such a configuration, IMD 14 can be configured to wake up periodically to listen to a communication request from external device 16.

In some examples, IMD 14 can be configured to transmit signals at varying signal transmission powers, also referred to in this disclosure as signal strengths. A signal strength can be increased or decreased by increasing or decreasing the amount of modulated electrical current at a transmit dipole, such as the transmit dipole of electrodes 61a and 61b. Varying signal strength used for transmission may allow IMD 14 to conserve battery power by transmitting at or near the minimum signal strength necessary for achieving a desired signal quality. For example, in response to an external device, such as external device 16, not being able to detect a signal from IMD 14, external device 16 can transmit an instruction to IMD 14. Upon receiving the instruction, processor 22 can cause communication module 42 to transmit future signals with a greater signal strength. Alternatively, if external device 16 is receiving a signal with a signal strength greater than is necessary for achieving a desired signal quality, then external device 16 can send an instruction to IMD 14, and upon receiving the instruction, processor 22 can cause communication module 42 to transmit future signals with a lower signal strength.

Power source 40 delivers operating power to various components of IMD 14. Power source 40 may include, for example, a small rechargeable or non-rechargeable battery and a power generation circuit to produce the operating power. In some examples, power requirements may be small enough to allow IMD 14 to utilize patient motion and implement a kinetic energy-scavenging device to trickle charge a rechargeable battery. In other examples, traditional batteries may be used for a limited period of time. As a further alternative, an external inductive power supply may transcutaneously power IMD 14 whenever measurements are needed or desired.

Figure 4:
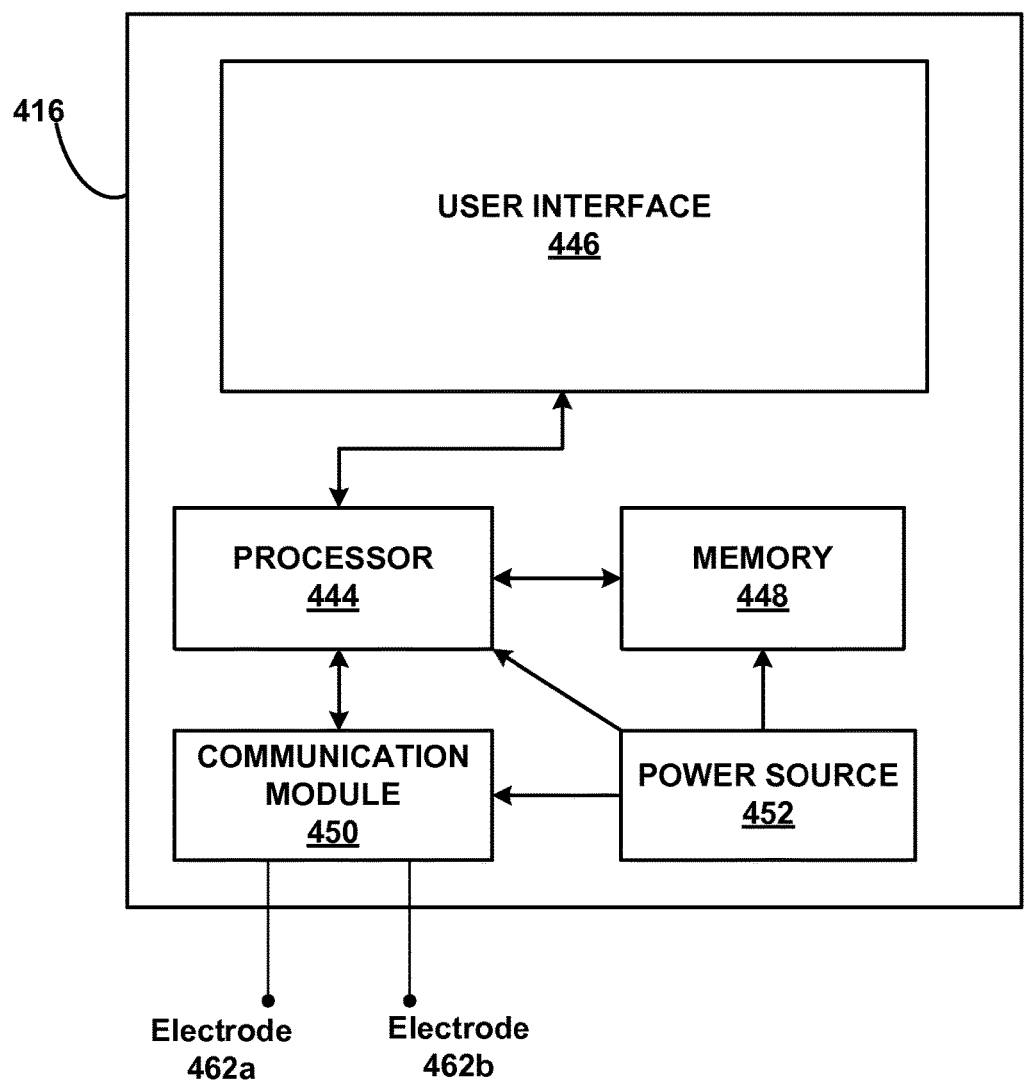
FIG. 4 is a block diagram illustrating an example of an external device configured to communicate bi-directionally with an IMD via TCC.

FIG. 4 is a functional block diagram illustrating various components of an external device 416 for programming and/or interrogating IMD 14. External device 416 may, for example, be the same device as external device 16 of FIG. 1. As shown in FIG. 4, external device 416 is an external display device that includes processor 444, memory 448, communication circuit 450, user interface 446, and power source 452. External device 416 may be embodied as a patient programmer or clinician programmer. A clinician or patient 12 interacts with user interface 446 in order to manually change the stimulation parameters of a program, change programs within a group, view therapy information, receive warnings or alerts, or otherwise interact with and control IMD 14. Generally, external device 416 configured as a clinician programmer would include additional features not provided on the patient programmer.

User interface 446 may include a screen or display and one or more input buttons that allow an external programmer to receive input from a user. Alternatively, user interface 446 may additionally or only utilize a touch screen display. The screen may be a liquid crystal display (LCD), dot matrix display, organic light-emitting diode (OLED) display, touch screen, or any other device capable of delivering and/or accepting information. For audible and/or tactile indications, such as an above threshold pressure, an external programmer may further include one or more audio speakers, voice synthesizer chips, piezoelectric buzzers, or the like.

Input buttons for user interface 446 may include a touch pad, increase and decrease buttons, emergency shut off button, and other buttons needed to control the delivery of drug therapy. Processor 444 controls user interface 446, retrieves data from memory 448 and stores data within memory 448. Processor 444 also controls the transmission of data through communication module 450 to IMD 14. Memory 448 includes operation instructions for processor 444 and data related to patient 12 therapy.

Communication module 450 allows the transfer of data to and from IMD 14 via TCC. Communication module 450 includes a pair of electrodes 462a and 462b configured to function as a dipole antenna and transmit and receive information encoded in electrical signals to and from IMD 14. These electrical signals are typically transmitted in a modulated format such as frequency shift keying, amplitude shift keying, phase shift keying, pulse width modulation, pulse amplitude modulation, quadrature amplitude modulation, orthogonal frequency division multiplexing, spread spectrum techniques, or in an analog signal format and/or modulation technique such as analog amplitude modulation or frequency modulation. In some implementations processor 444 may be able to adjust a signal strength parameter that determines a transmit signal strength for communication module 450

In one example, processor 444 controls communication module 450 to send and receive the information. User interface 446 may then update displayed information accordingly. Alternatively, communication module 450 may communicate with IMD 14 when signaled by a user through user interface 446. To support TCC, communication circuit 450 may include appropriate electronic components, such as amplifiers, filters, mixers, encoders, decoders, and the like that are not shown in FIG. 4. Power source 452 may be a rechargeable battery, such as a lithium ion or nickel metal hydride battery. Other rechargeable or conventional batteries may also be used. In some cases, an external programmer may be used when coupled to an alternating current (AC) outlet, i.e., AC line power, either directly or via an AC/DC adapter.

In some examples, external device 416 may be configured to recharge IMD 14 in addition to programming IMD 14. Alternatively, a recharging device may be capable of communication with IMD 14. Then, the recharging device may be able to transfer programming information, data, or any other information described herein to IMD 14. In this manner, the recharging device may be able to act as an intermediary communication device between an external programmer and IMD 14. In other cases, external device 16 may be integrated with a recharging functionality in the combined programming/recharging device. The techniques described herein may be communicated between IMD 14 via any type of external device capable of communication with IMD 14.

TCC can be utilized by external device 416 to communicate with IMD 14 by using electrical current pulses as information carriers. One electrode, such as electrode 462a can make physical contact with tissue of a patient at a first contact point, such as an arm or a leg, while the other electrode 462b makes contact with tissue of the patient at another contact point, such as the patient's opposite arm or leg or a point on the chest.

In some examples, as shown by the example wristband 18 of FIG. 1, one or both of electrodes 462a and 462b of external device 416 might take the form of conductive pads or wrist bands that make physical contact with a patient's wrists or arms. In some examples, as shown by patch 20 of FIG. 1, one or more of the electrodes 462a and 462b might take the form of electrocardiograph (ECG) pads that connect to a portion of a patient's body such as legs, chest, or shoulders. In other examples, one or more of electrodes 462a and 462b might take the form of batons, where a first baton electrically coupled to the first electrode 462a is held in a patient's first hand, and a second baton electrically coupled to the second electrode 462b is held in the patient's other hand. In another example, a patient may hold a single baton with one hand at each end. In the example, the first end can be electrically coupled to first electrode 462a, and the second end can be electrically coupled to second electrode 462b. In yet another example, the electrodes 42a-b might be part of a device that a patient stands on, such that a first footpad electrically coupled to the first electrode 462a is in contact with a patient's first foot and a second footpad electrically coupled to the second electrode 462b is in contact with the patient's second foot.

As discussed above in relation to equations 2 and 3, the signal strength received at electrodes 462a and 462b varies based on the length of the receive dipole and the angle of orientation between the transmit dipole and the receive dipole, both of which can be altered based on the location at which electrodes 462a and 462b make contact with patient 12. Due to variations in implant locations, implant orientations, and the geometries of individual patients, the receive dipole that works best for one patient may not work best for all patients. Accordingly, aspects of the present disclosure relate to determining an optimal receive dipole.

External device 416 can communicate bi-directionally with IMD 14. Therefore, depending on if external device 416 is receiving or transmitting data, electrodes 462a and 462b can function as either a receive dipole or a transmit dipole. External device 416 may be plugged into a wall or frequently recharged, and is therefore, not a power limited device like IMD 14. Not being a power limited device, or at least not as limited as IMD 14, external device 416 when transmitting data may be able to produce a transmit signal powerful enough to overcome some of the limitations discussed above, in the context of equations 2 and 3. Thus, when transmitting data to IMD 14, it is not always essential that external device 416 use the optimal transmit dipole. IMD 14, however, because of its size and power constraints, may benefit from being able to transmit data at the lowest signal strength detectable by external device 416. In order for IMD 14 to transmit at this potentially desirable low signal strength, an optimal receive dipole may need to be identified.

Figure 5:
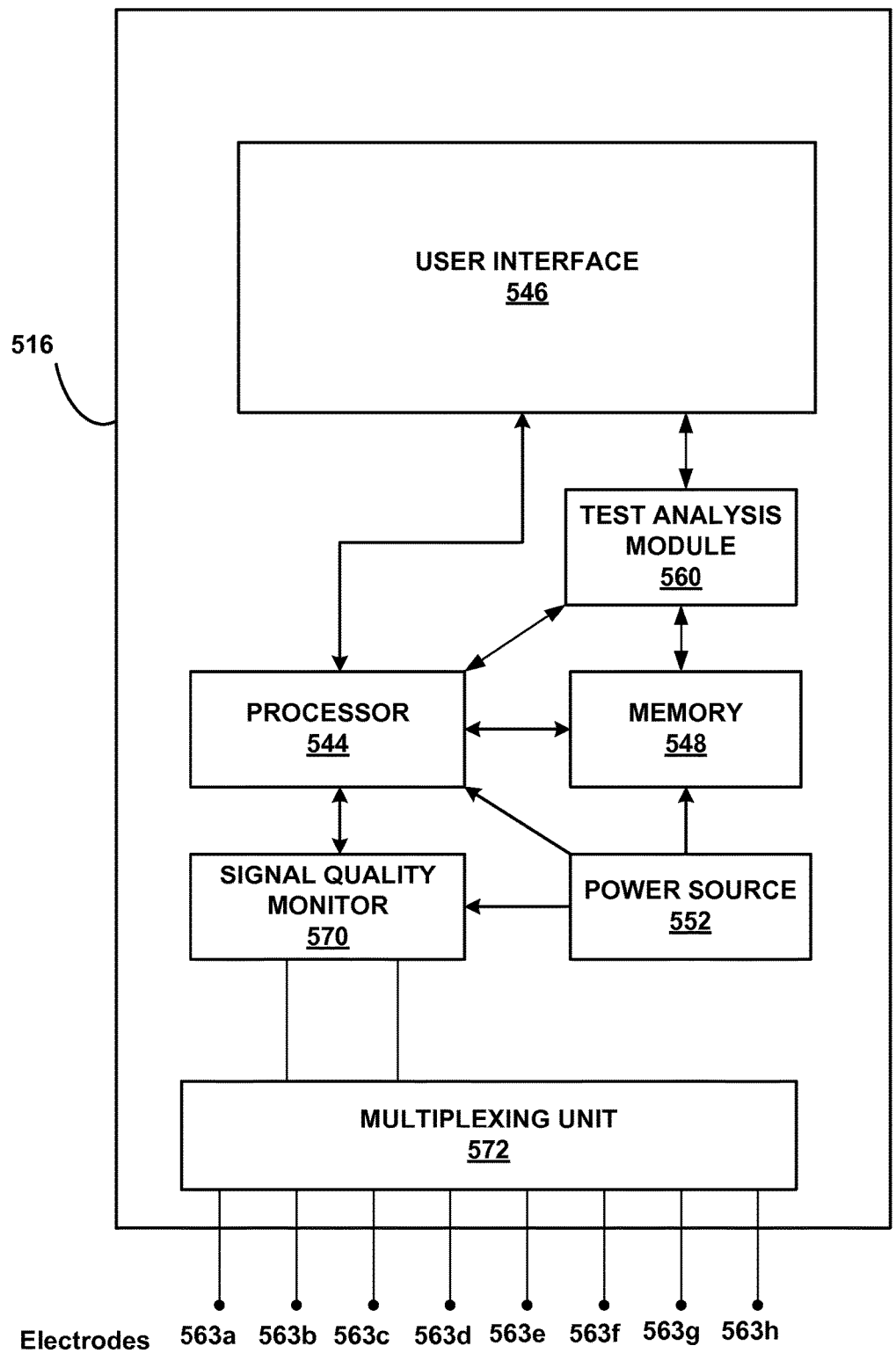
FIG. 5 is a block diagram illustrating an example of an external device configured to determine an optimal receive dipole in accordance with aspects of the present disclosure.

FIG. 5 is a functional block diagram illustrating various components of an external device 516 configured to determine an optimal receive dipole for facilitating TCC between an external device, such as external device 16 or 416, and IMD 14. As shown in FIG. 5, external device 516 is an external display device that includes processor 544, memory 548, signal quality monitor 570, multiplexing unit 572, user interface 546, a test analysis module 560, and power source 552. External device 516 may be embodied as a patient programmer or clinician programmer, or other computing device. In the present example, the functionality described in relation to FIGS. 4 and 5 are shown as being contained within different external devices (devices 416 and 516), but it is contemplated that the functionality described in relation to FIGS. 4 and 5 might be in a common device, or that the functionality of external device 516 may be added to external device 416 through an attachable or otherwise complimentary device. Furthermore, as will be discussed in more detail below, the functionality of FIGS. 4 and 5 may be incorporated into a wide array of different external device product types, such as a bathroom scales or hand held devices.

External device 516 of FIG. 5 includes a signal quality monitor 570 configured to measure the quality of a signal received from IMD 14 at electrodes 562a and 562b. Signal quality monitor 570 may, for example, measure the voltage difference between electrode 562a and 562b, where the measured voltage is indicative of signal strength. Signal quality may also be determined by signal quality monitor 570 based at least in part on a transmission power required for signal detection, a received signal strength, a received signal to noise ratio, a bit error rate, a data throughput rate, a data dropout rate, a background noise floor, an optimum frequency, or any combination of these measures.

To determine the optimal receive dipole, external device 516 can be configured to measure a signal quality for test signals received at multiple possible receive dipoles, and identify which of the multiple possible receive dipoles produce either adequate signal quality or the best signal quality. To test multiple possible receive dipoles, external device 516 can include a plurality of electrodes 563a-563h place in contact with different positions on an external skin surface of patient 12. The plurality of electrodes 563a-h can be electrically coupled to signal quality monitor 570 through multiplexing unit 572. Multiplexing unit 572 can make various combinations of electrodes 563a-563h either active or inactive. An electrode is active when it is in a state where a signal sensed at the electrode is received and processed by signal quality monitor 570. An electrode is inactive when it is either in a state where it is not attempting to receive a signal or when any signal received at the electrode is to be disregarded.

For testing a first possible receive dipole, only two of electrodes 563a-h might be active, while the others are inactive. For testing a second, different possible receive dipole, the active and inactive electrodes can be altered. When using external device 516 to determine an optimal receive dipole for a patient, electrodes 563a-h may, for example, be connected to the patient as follows:

electrode 563a connects to the patient's upper right chest;
electrode 563b connects to the patient's upper left chest;
electrode 563c connects to the patient's lower right chest;
electrode 563d connects to the patient's lower left chest;
electrode 563e connects to the patient's right wrist or hand;
electrode 563f connects to the patient's left wrist or hand;
electrode 563g connects to the patient's right ankle or foot; and
electrode 563h connects to the patient's left ankle or foot.

Throughout this disclosure, a receive dipole corresponding to electrodes 563a and 563b will be called the AB dipole, a receive dipole corresponding to electrodes 563c and 563d will be called the CD dipole and so on. In a first test, a test signal between electrodes 563a and 563b can be analyzed by signal quality monitor 570 to determine a signal quality for the test signal received using the AB dipole. A value indicative of that signal quality can be saved to memory 548. For a second test, a test signal between electrodes 563e and 563f can be analyzed by signal quality monitor 570 to determine a signal quality for the test signal received using the EF dipole. A value indicative of that signal quality can be saved to memory 548. In a third test, a test signal between electrodes 563e and 563d can be analyzed by signal quality monitor 570 to determine a signal quality for the test signal received using the ED dipole. A value indicative of that signal quality can be saved to memory 548. Although the present disclosure presents the tests of the various dipoles as being performed sequentially, it is contemplated that in some implementations multiple tests might be performed concurrently.

These three dipoles represent only a sampling of the possible receive dipoles that can be tested to determine the optimal receive dipole. Any two of electrodes 563a-h can be made active for any particular test, and a signal quality for a test signal received across that dipole can be determined by signal quality monitor 570. Thus, using the 8-electrode example of FIG. 5, the dipoles that can be tested include AB, AC, AD, AE, AF, AG, AH, BA, BC, BD, BE, BF, BG, BH, CA, CB, CD, CE, CF, CG, CH, DA, DB, DC, DE, DF, DG, DH, EA, EB, EC, ED, EF, EG, EH, FA, FB, FC, FD, FE, FG, FH, GA, GB, GC, GD, GE, GF, GH, HA, HB, HC, HD, HE, HF, and HG. In some configurations, not every possible dipole needs to be tested. For example, due to their symmetrical nature, the EB dipole and the BE dipole should result in the same signal strength and overall signal quality, thus only one test needs to be performed. It is also contemplated that in some configurations, external device 516 might have more or fewer than the eight electrodes shown in FIG. 5.

In one configuration, external device 516 can send a high powered signal to IMD 14 instructing IMD 14 to enter a test mode. In the test mode, IMD 14 can send out a test signal or plurality of test signals known to external device 516. External device 516 can be configured to identify a test signal using known telemetry techniques, such as cross-correlation, and once identified, a signal quality of the test signals received at pairs of electrodes 563a-h can be measured by signal quality monitor 570. A value indicating the signal quality for a particular receive dipole can be stored in memory 548.

As used in this disclosure, a test signal does not necessarily have to be a signal that is different than a signal IMD 14 might transmit in its normal course of operation, such as during a communication session with external device 516. For example, aspects of the techniques of this disclosure may be able to be applied to signals received in the normal course of operation for IMD 14, in which case any signal transmitted by IMD 14 might be able to be used as a test signal. In other examples, however, test signals might refer to signals that are specifically configured to enable the techniques of this disclosure. For example, as discussed elsewhere in this disclosure, a test signal may include in a data header or data packet, information identifying a signal type, such as high powered or low powered, or information identifying from which dipole the test signal was transmitted.

In some configurations, when operating in the test mode, IMD 14 may send multiple types of test signals, such as a low power signal, a medium power signal, and a high power signal. The type of test signal may, for example, be identified to external device 516 in a data header or data packet of the signal. For example, the three example types of signals given above could be communicated to external device 516 using a two bit flag in the header of a data packet, where 00 represents a first signal type, 01 represents a second signal type, and 10 represents a third signal type. A fourth signal type could also be represented with the two bits 11, if a fourth signal type were utilized. Signal quality monitor 570 can determine a signal quality for each type of signal and values indicating the signal quality for each type of signal can be stored in memory 548.

Test analysis module 560 can analyze the test results stored in memory 548 and present the signal quality test results to a user of external device 516 in multiple forms. For example, test analysis module 560 might classify the different possible dipoles based on the measured signal quality according to a certain level of granularity. A first level of granularity might include classifying each dipole as either "adequate" or "inadequate," while a higher level of granularity might include classifying each dipole as "poor," "average," "good," or "excellent." A yet higher level of granularity might include assigning each dipole a score between zero and ten or zero and one hundred. As the orientation of an IMD generally does not change and the geometry of a patient's body generally does not change significantly over time, a receive dipole will generally maintain the same quality of transmission throughout the time the IMD is implanted. For example, if a particular dipole is determined to be "poor" or "excellent" shortly after implantation, it will likely remain "poor" or "excellent," respectively, for as long as the IMD is implanted in the patient. In a configuration where IMD 14 sends multiple types of test signals, test analysis module 560 can present to the user the results for each signal type. For example, a particular dipole may be "poor" when using the low power signal but "average" when using the medium power signal.

Based on the results of the test, a user of external device 516 can identify an optimal receive dipole that can be used for TCC between external devices 16 or 416 and IMD 14. Knowing the optimal receive dipole can improve the user experience in several ways. For example, once the optimal receive dipole is known, the patient can more quickly connect the electrodes of the external device for future communication sessions, decreasing the time and amount of experimentation needed to establish a communication session. Additionally, for IMDs, such as IMD 14, that can transmit at varying powers, a clinician or technician may be able to reduce the transmit power of IMD 14 if a particular dipole produces signal quality that is greater than needed for a particular application, thus saving battery power. Alternatively, based on factors such as battery capacity and implant duration, a clinician may determine that increasing the transmit power to enable communication over a preferred dipole, such as hand to hand, may be acceptable.

Additionally, knowing the optimal receive dipole can aide a user of external device 516 in determining a product type that might be suitable for external device 416. For example, a first product type embodying external device 416 might utilize batons that a patient grabs, while a second product type utilizes footpads a patient stands on, and a third product type utilizes ECG patches that connect to a patient's chest. Based on the tests performed by external device 516, it can be determined whether a particular product type is suitable for a particular patient. For example, if the tests of external device 516 show that the EF receive dipole (hand to hand, or wrist to wrist) produces poor signal quality, then the first product type might not be a good option for the patient. Conversely, if the GH receive dipole (foot to foot) produces good signal quality, the second product type might be a good option for the patient. Patients generally prefer a product type for external device 416 that does not require them to disrobe, and thus, may prefer a product type that is configured to utilize a limb contact point, such as at a patient's arms or legs over a device that requires chest contact points. External device 516 can aid the patient in finding an appropriate product type for external device 416.

Figure 6:
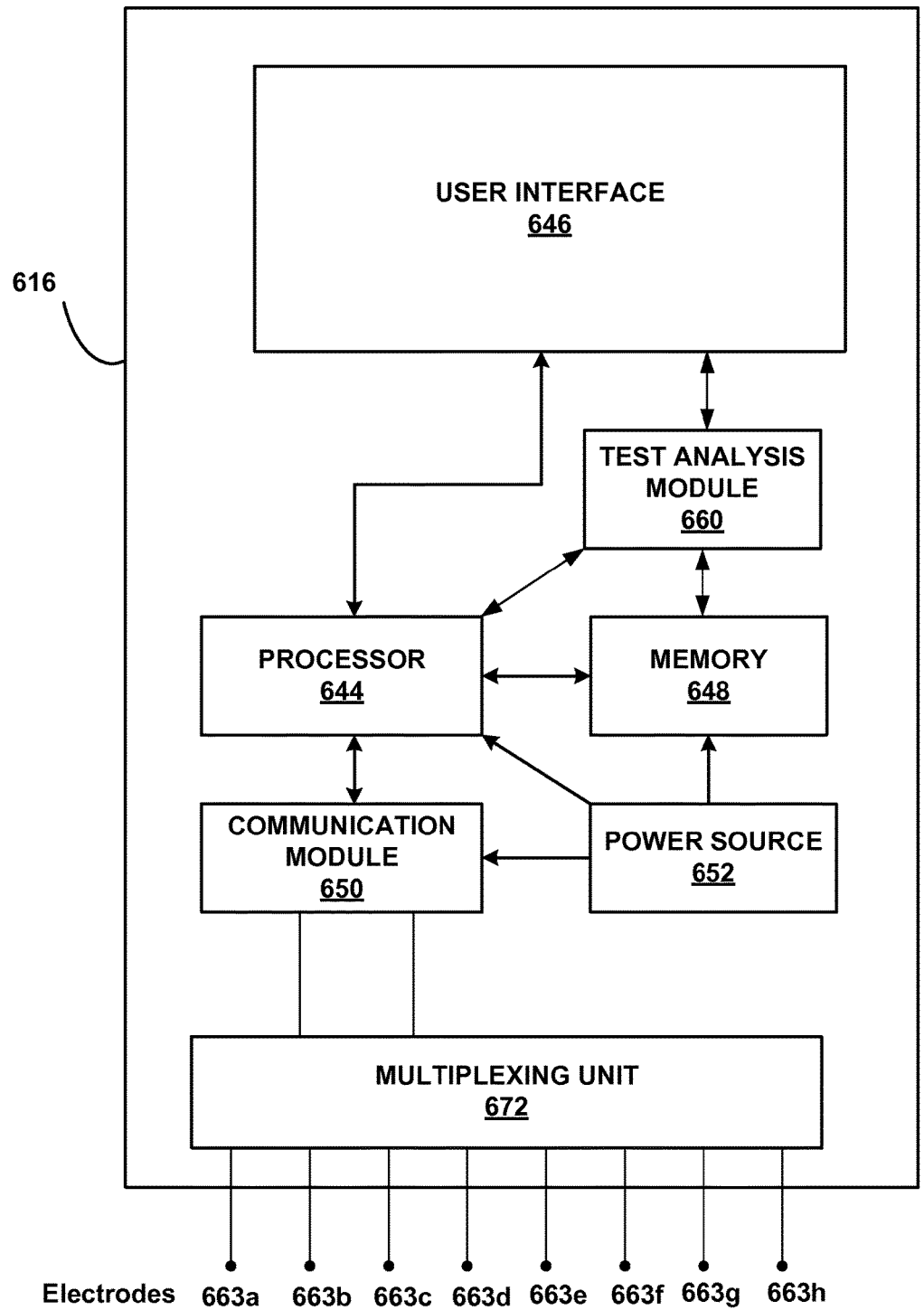
FIG. 6 is a block diagram illustrating an example of an external device configured to determine an optimal receive dipole in accordance with aspects of the present disclosure.

FIG. 6 is a functional block diagram illustrating various components of an external device 616 configured to determine an optimal receive dipole for facilitating TCC between an external device, such as external devices 16 and 416, and IMD 14. FIGS. 4, 5, and 6 are shown as being contained within different external devices (devices 416, 516, and 616), but it is contemplated that the functionality described in relation to FIGS. 4, 5, and 6 might be in a common device, or that the functionality of external device 616 may be added to external device 416 or 516 through an attachable or otherwise complimentary device. Furthermore, as will be discussed in more detail below, the functionality of FIGS. 4, 5, and 6 may be incorporated into a wide array of different external device product types, such as a bathroom scales or hand held devices.

As shown in FIG. 6, external device 616 is an external display device that includes processor 644, memory 648, communication module 650, multiplexing unit 672, user interface 646, a test analysis module 660, and power source 652. Unless explicitly stated to the contrary, it can be assumed that communication module 650 can include the same functionality described above for communication module 550, test analysis module 660 can include the same functionality is test analysis module 560, and so on. External device 616 may be embodied as a patient programmer or clinician programmer. While the external device 516 of FIG. 5 is configured to determine an optimal receive dipole by measuring the signal quality of test signals received from IMD 14 for various receive dipoles, external device 616 is configured to determine an optimal receive dipole by transmitting a plurality of test signals from various transmit dipoles. The signal quality of the various test signals can then be measured at IMD 14, and the results can be returned to external device 616. Due to reciprocity, the best transmit dipole will also be the best receive dipole, and the weakest transmit dipole will also be the weakest receive dipole. Therefore, by knowing a measured signal quality for a transmit dipole, the suitability of the dipole for receiving can also be determined.

External device 616 includes a communication circuit configured to transmit test signals in the form of a current driven across two of electrodes 663-*ah*. To test multiple possible transmit dipoles, external device 16 can include a plurality of electrodes 663*a*-663*h*. The plurality of electrodes 663*a-h* can be electrically coupled to communication module 650 through multiplexing unit 672. Multiplexing unit 672 can make two of electrodes 663*a*-663*h* active at a particular time and the remaining of electrodes 663*a-h* inactive. In this particular context, a pair of electrodes are active when a current is being driven across the pair of electrodes by communication module 650, and a pair of electrodes are inactive when a current is not being driven across the pair of electrodes by communication module 650.

For testing a first possible transmit dipole, only two of electrodes 663a-h might be active, while the others are inactive. For testing a second, different possible transmit dipole, the active and inactive electrodes can be altered. When using external device 616 to determine an optimal transmit dipole for a patient, electrodes 663a-h may, for example, be connected to the patient as follows:

electrode 663a connects to the patient's upper right chest;
electrode 663b connects to the patient's upper left chest;
electrode 663c connects to the patient's lower right chest;
electrode 663d connects to the patient's lower left chest;
electrode 663e connects to the patient's right wrist or hand;
electrode 663f connects to the patient's left wrist or hand;
electrode 663g connects to the patient's right ankle or foot; and
electrode 663h connects to the patient's left ankle or foot.

As previously used in reference to FIG. 5, a transmit dipole corresponding to electrodes 663a and 663b will be called the AB dipole, a transmit dipole corresponding to electrodes 663c and 663d will be called the CD dipole and so on. In a first test, a signal can be transmitted from electrodes 663a and 663b to IMD 14 and can be analyzed by a signal quality monitor at IMD 14 to determine a signal quality for a signal received using the AB dipole. A value indicative of that signal quality can be saved to memory 34. For a second test, a signal can be transmitted from electrodes 563e and 563f and can be analyzed by signal a quality monitor at IMD 14 to determine a signal quality for a signal received using the EF dipole. A value indicative of that signal quality can be saved to memory 34. In a third test, a signal can be transmitted from electrodes 563e and 563d to IMD 14 and can be analyzed by a signal quality monitor at IMD 14 to determine a signal quality for a signal received using the ED dipole. A value indicative of that signal quality can be saved to memory 34.

These three dipoles represent only a sampling of the possible transmit dipoles that can be tested to determine the optimal transmit dipole. A signal can be transmitted from any pair of electrodes 663a-h. Thus, using the 8-electrode example of FIG. 6, the dipoles that can be tested include AB, AC, AD, AE, AF, AG, AH, BA, BC, BD, BE, BF, BG, BH, CA, CB, CD, CE, CF, CG, CH, DA, DB, DC, DE, DF, DG, DH, EA, EB, EC, ED, EF, EG, EH, FA, FB, FC, FD, FE, FG, FH, GA, GB, GC, GD, GE, GF, GH, HA, HB, HC, HD, HE, HF, and HG. In some configurations, not every possible dipole needs to be tested. For example, due to their symmetrical nature, the EB dipole and the BE dipole should result in the same signal strength, thus only one of the two needs to be tested. It is also contemplated that in some configurations, external device 616 might have more or fewer than the eight electrodes shown in FIG. 6.

External device 616 can send a high powered signal to IMD 14 instructing IMD 14 to enter a test mode. In the test mode, IMD 14 can measure the signal quality of test signals transmitted from external device 616 and store values for the signal quality in memory 34. IMD 14 can be configured to identify a test signal using known telemetry techniques, and once identified, a signal quality received at electrodes 61a and 61b can be measured by a signal quality monitor for a plurality of the possible transmit dipoles. In one example, each test signal might include a unique signal identification that associates the signal with a particular dipole. For example, each test signal might include in a header or data packet, a codeword that associates the signal a particular transmit dipole. Values indicating the signal quality of the various transmit dipoles can be stored in memory 34 and then at the conclusion of the testing be sent to external device 616. Using the signal identification of each test signal, the values indicating the signal quality can be associated with the transmit dipole used to produce that signal quality.

In some configurations, when operating in the test mode, external device 616 may send multiple types of test signals to IMD 14, such as a low power signal, a medium power signal, and a high power signal. The type of test signal may, for example, be identified to IMD 14 in a data header or data packet of the signal. A signal quality monitor at IMD 14 can determine a signal quality for each type of signal and values indicating the signal quality for each type of signal can be stored in memory 34.

The results of the tests can be presented to a user of external device 616 in multiple forms. For example, external device 616 might classify the different possible dipoles based on the measured signal qualities according to a certain level of granularity. A first level of granularity might include classifying each dipole as either "adequate" or "inadequate," while a higher level of granularity might include classifying each dipole as "poor," "average," "good," or "excellent." A yet higher level of granularity might include assigning each dipole a score between zero and ten or zero and one hundred or a binary numbering scheme. As the orientation of an IMD generally does not change and the geometry of a patient's body generally does not change significantly over time, a transmit dipole will generally maintain the same quality of transmission throughout the time the IMD is implanted. For example, if a particular dipole is determined to be "poor" or "excellent" shortly after implantation, it will likely remain "poor" or "excellent," respectively, for as long as the IMD is implanted in the patient.

Based on the results of the test, a user of external device 616 can identify the optimal dipoles that can be used for TCC between external device 616 and IMD 14. Knowing the optimal transmit dipole or dipoles can improve the user experience in several ways. For example, once the optimal transmit dipole is known, the patient can more quickly connect the external device for future communication sessions.

Additionally, as will be described in more detail below with reference to the example of FIG. 7, external devices, such as the external device of FIG. 4, can be included in a number of different external device product types, which might be configured for hand use, feet use, chest use, or any combination thereof. Many external device product types require a specific contact point on a patient, such as a hand or a foot. If during testing it is found that a specific contact point, such as a hand, does not a produce a suitable transmit dipole for a particular patient, then the user of external device 616 can know to avoid using with that patient an external device product that requires contact with the patient's hand. Similarly, if a particular external device product requires contact with a patient's feet, but the transmit dipole between the left foot and right foot is inadequate for TCC, then the user of external device 616 knows to avoid using that particular external device product type with the patient.

Figure 7:
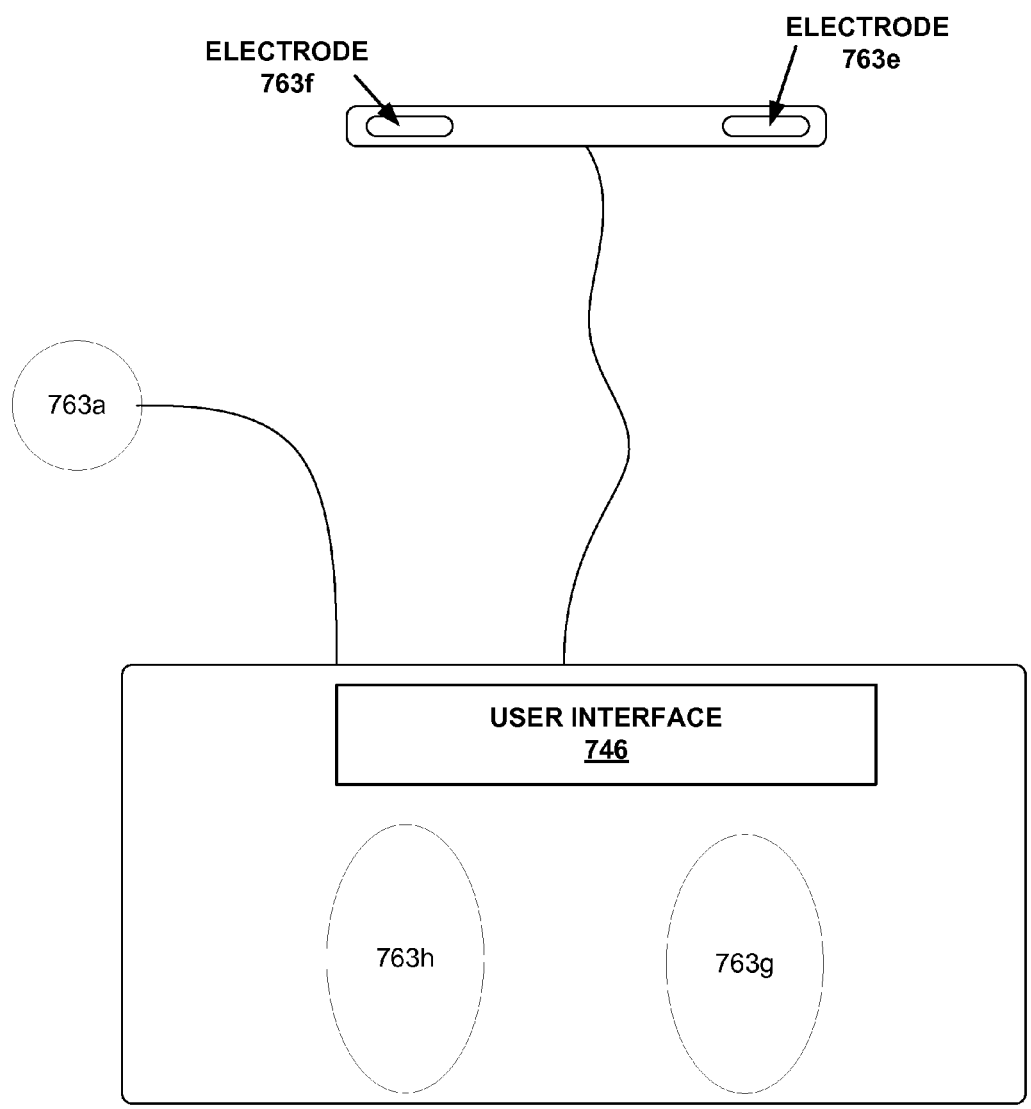
FIG. 7 is a block diagram illustrating an example of an external device configured to determine an optimal receive dipole in accordance with aspects of the present disclosure.

FIG. 7 shows a block diagram of an external device 719 similar to a personal bathroom scale. Device 719 is configured to have both the functionality of external device 416 of FIG. 4 and either or both of devices 516 or 616 of FIGS. 5 and 6, respectively. Thus although certain components, such as signal quality monitor, communication module, memory, power source, and others are not explicitly shown in FIG. 7, it is contemplated that any aspect of FIGS. 4, 5, and 6 described above could be implemented into device 719. Device 719 includes a user interface and a plurality of electrodes 763a, e, f, g, h. Electrodes 763h and 763g are electrically conductive footpads a user can stand on. In the example of FIG. 7, electrodes 763f and 763e are conductive ends of a baton, but may also, in other configurations, be any type of handheld electrode. Electrode 763a is a chest patch configured to be attached to a patient's chest. As described in more detail in FIGS. 5 and 6, each of electrodes 763a, e, f, g, h can be made either active or inactive to create a plurality of different receive or transmit dipoles.

When using external device 719, for example, electrodes 763a, e, f, g, h may be connected to a patient as follows:
electrode 1063h touches a patient's left foot;
electrode 1063g touches the patient's right foot;
electrode 1063f is held in the patient's left hand;
electrode 1063e is held in the patient's right hand; and
electrode 1063a is connected to the patient's chest.

As previously used in reference to FIGS. 5 and 6, a transmit or receive dipole corresponding to electrodes 763f and 763e will be called the FE dipole, a transmit or receive dipole corresponding to electrodes 763a and 763f will be called the AF dipole and so on. As discussed previously in relation to FIGS. 5 and 6, device 719 may test a first dipole of the plurality of dipoles by making two of electrodes 763a, e, f, g, h active and the remainder inactive, and then testing a second dipole by changing which electrodes are active and which are inactive. Device 719 may, in some configurations, include a test mode that first determines a signal quality for the different dipoles that can be created by the foot and hand electrodes (i.e. electrodes 763e-h), which might include the EF, EG, EH, FE, FG, FH, GE, GF, GH, HE, HF, and HG dipoles.

After testing the dipoles, device 719 may automatically initiate a communication session with IMD 14 using the dipole with the highest measured signal quality. In such a configuration, a user may not necessarily know which dipole is being used for the communication session, but the use of the dipole with the highest measured signal quality may improve the user experience by successfully establishing a communication session with minimal effort or experimentation required by the user. In other configurations, device 719 may present the results of the test to the user for use in future communication sessions. For example, if the GH dipole provides sufficient signal quality between device 719 and IMD 14, then for future communication sessions, the user may be able to establish a communication session, without entering a test mode, simply by stepping on the foot electrodes (i.e. electrodes 763h and 763g).

Device 719 may also include one or more patch electrodes, such as electrode 763a, for attaching to a user's chest. Electrode 763a may be used with any of electrodes 763e-h to form additional receive dipoles to be tested. In one configuration, device 719 may first test dipoles for electrodes 766e-h, and then instruct a user to attach electrode 763a to his chest in response to electrodes 763e-h not producing a dipole with adequate signal quality.

Figure 8:
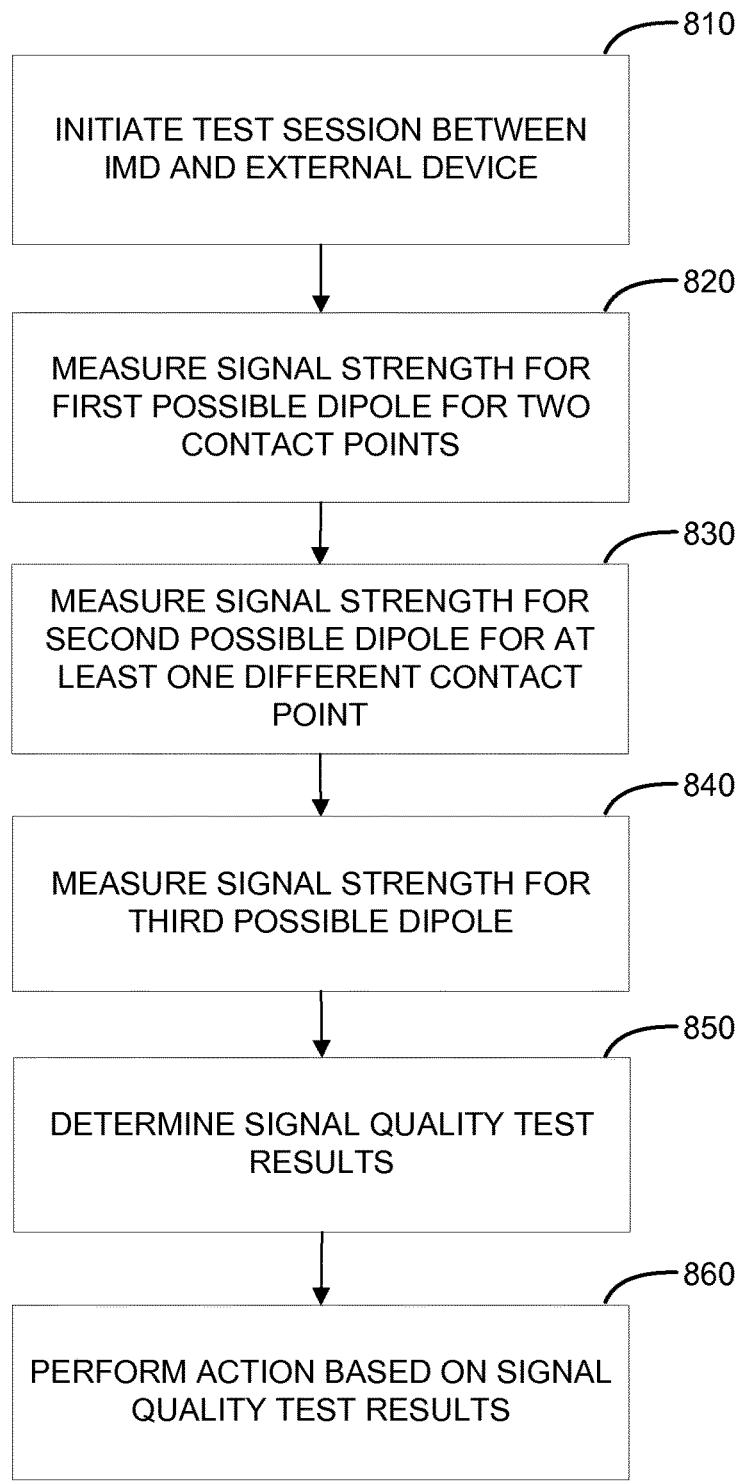
FIG. 8 is a flowchart showing an example method of using an external device and an IMD according to techniques of this disclosure.

FIG. 8 shows a flowchart of an example method of using a medical system comprising an IMD and an external device, such as the IMD 14 and external device 16 of FIG. 1, or any of external devices 516, 616, or 716 of FIGS. 5, 6, and 7, respectively. A test session can be established between IMD 14 and an external device (block 810). The test session may, for example, be initiated by having the external device transmit a high powered test initiation signal to the IMD.

Once the test session is established, a plurality of possible receive dipoles can be tested. As discussed above in relation to FIG. 5, the possible receive dipoles can be tested by measuring, at external device 516, a signal quality of a test signal transmitted from IMD 14 to external device 516. Alternatively, as discussed above in relation to FIG. 6, the possible receive dipoles can be tested by measuring, at IMD 14, a signal quality of a test signal transmitted from external device 616 to IMD 14. The testing can include measuring a signal quality, using for example a signal quality monitor such as signal quality monitor 570 or a signal quality monitor in communication module 42, for a first possible dipole, where the first possible dipole is defined by two electrodes on a patient (block 820). The testing can further include measuring a signal quality for a second possible dipole, where the second possible dipole is defined by two electrodes on the patient, and at least one of the electrodes is different than the electrodes of the first possible dipole (block 830). The testing can further include measuring a signal quality for a third possible dipole, where the third possible dipole is defined by two electrodes on the patient, and the two electrodes are different than the two electrodes of the first possible dipole and the two electrodes of the second possible dipole (block 840). A test analysis module, such as test analysis module 560 or 660, can determine signal quality test results based on the testing of the first, second, and third dipole (block 850). An external device can perform an action or actions based on the determined signal quality test results (block 860). Actions may, for example, include initiating a communication session, identifying a dipole that provides at least a minimum signal quality with the IMD, and presenting information to a user of the external device. The actions performed by the external device may alternatively or additionally include having the external device sending an instruction to IMD 14 to transmit future signals at a greater signal strength or a lower signal strength.

In some examples, if the signal quality test results indicate that none of the possible dipoles are suitable for a communication session due to either inadequate signal strength or an inadequate signal-to-noise ratio, then the action may include initiating a retest of the possible dipoles. For example, the possible dipoles may be retested with IMD 14 transmitting at a greater signal strength, or the possible dipoles may be retested with the electrodes at different contact points on the patient. The action may also include initiating a trouble shooting routine that instructs the user of an external device to perform a series of tests to ensure that the external device is functioning properly and is being used properly.

In this disclosure, the terms module, and unit have been used to emphasize functional aspects of described devices. These terms, however, do not necessarily require that separately described modules or units be realized by different hardware units within a device. For example, functionality ascribed to a particular unit or module in this disclosure may in fact be implemented in hardware, software, firmware, or any combination thereof, while functionality ascribed to a different unit or module may be implemented by a similar or different combination of hardware, software, or firmware.

Accordingly, certain aspects of the techniques described herein may be implemented in hardware, software, firmware, or any combination thereof. Any features described as modules or components may be implemented together in an integrated logic device or separately as discrete but interoperable logic devices. If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The techniques additionally, or alternatively, may be realized at least in part by a computer-readable communication medium that carries or communicates code in the form of instructions or data structures and that can be accessed, read, and/or executed by a computer.

The code may be executed by one or more processors, such as one or more digital signal processors (DSPs), general purpose microprocessors, an application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated software modules or hardware modules configured for encoding and decoding, or incorporated in a combined video encoder-decoder (CODEC). Also, the techniques could be fully implemented in one or more circuits or logic elements.

Various embodiments of the invention have been described. These and other embodiments are within the scope of the following claims.

The invention claimed is:

1. An external device comprising:
a plurality of three or more electrodes positionable at different tissue contact points on an external tissue surface of a patient;
a communication unit configured to communicate with an implantable medical device via a plurality of dipoles formed by different combinations of two of the three or more electrodes, wherein the communication unit is further configured to transmit a signal causing the implantable medical device to enter a test mode;
a processor configured to identify a dipole that provides at least a minimum signal quality with the implantable medical device, wherein the processor identifies the dipole that provides the at least minimum signal quality based on one or more test signals generated during the test mode; and
a test analysis module configured to present to a user an indication of the dipole identified based on the one or more test signals.

2. The external device of claim 1, wherein the communication unit is configured to transmit the one or more test signals using the plurality of dipoles.

3. The external device of claim 2, wherein the processor is configured to identify the dipole that provides at least the minimum signal quality with the implantable medical device based at least in part on signal quality test results transmitted from the implantable medical device.

4. The external device of claim 2, wherein the processor is configured to identify the dipole that provides at least the minimum signal quality with the implantable medical device based at least in part on a signal from the implantable medical device identifying the dipole that provides at least the minimum signal quality with the implantable medical device.

5. The external device of claim 1, wherein the communication unit is configured to receive the one or more test signals from the implantable medical device using the plurality of dipoles.

6. The external device of claim 5, wherein the processor is configured to identify the dipole that provides at least the minimum signal quality with the implantable medical device based at least in part on the one or more test signals received from the implantable medical device.

7. The external device of claim 1, wherein the one or more test signals comprise signals transmitted at different power levels, and wherein the processor is further configured to identify the dipole that provides the at least minimum signal quality with the implantable medical device based at least in part on a power level of the dipole that provides at least the minimum signal quality.

8. A medical device system comprising:
an implantable medical device (IMD) comprising:
a first communication unit;
a first processor;
an external device comprising:
a plurality of three or more electrodes positionable at different tissue contact points on an external tissue surface of a patient;
a second communication unit configured to communicate with the IMD via a plurality of dipoles formed by different combinations of two of the three or more electrodes, wherein the second communication unit is further configured to transmit a signal causing the implantable medical device to enter a test mode; and
a second processor configured to identify a dipole that provides at least a minimum signal quality with the IMD, wherein the processor identifies the dipole that provides the at least minimum signal quality based on one or more test signals generated during the test mode, wherein the processor is further configured to present to a user an indication of the dipole identified based on the one or more test signals.

9. The medical device system of claim 8, wherein the second communication unit is configured to transmit, to the IMD, the one or more test signals using the plurality of dipoles.

10. The medical device system of claim 9, wherein the second processor is configured to identify the dipole that provides at least the minimum signal quality with the IMD based at least in part on signal quality test results received from the IMD.

11. The medical device system of claim 9, wherein the first processor is configured to identify the dipole that provides at least the minimum signal quality with the IMD based at least in part on the test signals, and the first communication unit is configured to transmit to the external device an indicator of the dipole that provides at least the minimum signal quality with the 1 MB.

12. The medical device system of claim 8, wherein the first communication unit is configured to transmit the one or more test signals to the external device, and the second communication unit is configured to receive the one or more test signals via the plurality of dipoles formed by different combinations of the electrodes.

13. The medical device system of claim 12, wherein the second processor is configured to identify the dipole that provides at least the minimum signal quality with the IMD based at least in part on the one or more test signals received from the IMD.

14. The medical device system of claim 8, wherein the external device is configured to transmit to the 1 MB an instruction, and in response to receiving the instruction, the first communication unit is configured to either increase or decrease a signal transmission power.

15. The medical device system of claim 8, wherein
the first communication unit is configured to
  receive, from the external device, the one or more test signals via the plurality of dipoles formed by different combinations of electrodes;
  identify within each test signal, a signal identification for the test signals; and
wherein the IMD further comprises:
  a signal quality monitor configured to determine a signal quality for each test signal;
  a communication transmitting unit configured to transmit, to the external device, an indicator of at least one signal identification for at least one test signal.

16. The medical device system of claim 8, wherein the one or more test signals comprise signals transmitted at different power levels, and wherein the second processor is further configured to identify the dipole that provides the at least minimum signal quality with the implantable medical device based at least in part on a power level of the dipole that provides at least the minimum signal quality.

17. A method comprising:
  transmitting a signal causing an implantable medical device (IMD) to enter a test mode;
  communicating with the IMD via a plurality of dipoles formed by different combinations of two electrodes positioned at different tissue contact points on an external tissue surface of a patient, wherein the different combinations of two electrodes are formed from a plurality of three or more electrodes;
  identifying a dipole that provides at least a minimum signal quality with the implantable medical device based on one or more test signals generated during the test mode; and
  presenting to a user an indication of the dipole identified based on the one or more test signals.

18. The method of claim 17, wherein the communicating comprises transmitting the one or more test signals to the IMD using the plurality of dipoles.

19. The method of claim 18, further comprising:
  receiving signal quality test results from the IMD; and
  wherein the identifying the dipole that provides at least the minimum signal quality with the implantable medical device is based at least in part on the signal quality test results.

20. The method of claim 18, further comprising:
  receiving, from the IMD, a signal identifying the dipole that provides at least the minimum signal quality.

21. The method of claim 17, further comprising:
  wherein the communicating comprises receiving the one or more test signals from the IMD using the plurality of dipoles.

22. The method of claim 21, further comprising
  wherein the identifying the dipole that provides at least the minimum signal quality with the IMD is based at least in part on the one or more test signals received from the implantable medical device.

23. The method of claim 17, wherein the one or more test signals comprise signals transmitted at different power levels, and wherein the method further comprises:
  identifying the dipole that provides the at least minimum signal quality with the implantable medical device based at least in part on a power level of the dipole that provides at least the minimum signal quality.

\* \* \* \* \*